United States Patent
Oyaizu

(10) Patent No.: US 9,510,751 B2
(45) Date of Patent: Dec. 6, 2016

(54) OCULAR CHARACTERISTIC DEVICE TO ELIMINATE GHOSTING FROM AN IOL DURING CORNEAL CURVATURE MEASUREMENT

(71) Applicant: CANON KABUSHIKI KAISHA, Tokyo (JP)

(72) Inventor: Keisuke Oyaizu, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 160 days.

(21) Appl. No.: 14/278,927

(22) Filed: May 15, 2014

(65) Prior Publication Data
US 2014/0340635 A1 Nov. 20, 2014

(30) Foreign Application Priority Data
May 16, 2013 (JP) ................. 2013-104247

(51) Int. Cl.
A61B 3/107 (2006.01)
A61B 3/15 (2006.01)
A61B 3/12 (2006.01)
A61B 3/10 (2006.01)
A61B 3/14 (2006.01)
A61B 3/11 (2006.01)
A61B 3/00 (2006.01)

(52) U.S. Cl.
CPC ............ *A61B 3/107* (2013.01); *A61B 3/0091* (2013.01); *A61B 3/1005* (2013.01); *A61B 3/112* (2013.01); *A61B 3/12* (2013.01); *A61B 3/14* (2013.01); *A61B 3/156* (2013.01)

(58) Field of Classification Search
CPC ............ A61B 3/107; A61B 3/12; A61B 3/14; A61B 3/112; A61B 3/0091; A61B 3/1005; A61B 3/156
USPC ................. 351/207, 221, 211, 212
See application file for complete search history.

(56) References Cited

U.S. PATENT DOCUMENTS

| 5,212,507 A * | 5/1993 | Fujieda | A61B 3/107 351/212 |
| 5,500,696 A * | 3/1996 | Masuda | A61B 3/107 351/205 |
| 7,123,751 B1 * | 10/2006 | Fujieda | A61B 5/117 340/5.53 |

FOREIGN PATENT DOCUMENTS

JP 3244873 B2 1/2002

* cited by examiner

*Primary Examiner* — Zachary Wilkes
(74) *Attorney, Agent, or Firm* — Canon U.S.A., Inc. IP Division

(57) ABSTRACT

If an intraocular lens is inserted in an eye to be examined, characteristics of the eye to be examined are measured after increasing light intensity of visible light projected onto the eye to be examined to be higher than light intensity at the time of measurement of an eye to be examined in which no intraocular lens is inserted.

13 Claims, 12 Drawing Sheets

OCULAR CHARACTERISTIC DEVICE TO ELIMINATE GHOSTING FROM AN IOL DURING CORNEAL CURVATURE MEASUREMENT

BACKGROUND

Field of Art

The present disclosure relates to an ocular characteristics measuring apparatus for measuring ocular characteristics of an eye to be examined.

Description of the Related Art

Recently, an increasing number of eyes to be examined have intraocular lenses inserted therein as intraocular lenses (IOL) for cataract operation have become widely used. Hereafter, an intraocular lens is referred to as an "IOL" and the eye to be examined in which an intraocular lens is inserted is referred to as an "IOL eye." The IOL differs from the crystalline lenses in characteristics, such as shape, material and existence of refractive power adjustability. Therefore, in order to measure the IOL eye with high precision, it is necessary to use a measuring method in consideration of characteristics of the IOL eye.

Japanese Patent No. 3244873 proposes a technique about an eye refractivity measuring apparatus in which an examiner inputs, into the apparatus, whether an eye to be examined is an IOL eye, and the device switches functions of a jog dial in accordance with the input. Therefore, the examiner may adjust light intensity of a fixation target using the jog dial with respect to the IOL eye which is typically subject to contraction.

Techniques to avoid contraction of the pupil have been proposed to prevent making measurement of ocular refractivity difficult.

SUMMARY

At the time of the measurement of a cornea surface curvature, if the pupil is fully open, measurement light is reflected on the IOL and forms a ghost. Therefore, there is a possibility that measurement accuracy is lowered. However, when contraction is caused, a light flux which forms the ghost is blocked by the iris and thus the ghost is eliminated.

The present disclosure eliminates the ghost at the time of the measurement of the cornea surface curvature of the IOL eye.

In order to solve the problem described above, an ocular characteristics measuring apparatus of the present disclosure includes:

a first projecting unit configured to project a light flux onto a cornea of an eye to be examined from the outside of a central axis of an optical path;

a light receiving unit configured to receive a corneal reflection light flux by the first projecting unit;

a first calculating unit configured to calculate a cornea surface curvature in accordance with an corneal reflection image received from the light receiving unit;

a second projecting unit configured to project visible light onto the eye to be examined; and a control unit configured to change light intensity of the visible light projected by the second projecting unit, wherein, if an intraocular lens is inserted in the eye to be examined, the control unit increases light intensity of the visible light projected by the second projecting unit to be higher than the light intensity of visible light to be projected onto an eye to be examined in which no intraocular lens is inserted; and wherein the first calculating unit calculates the cornea surface curvature in accordance with the corneal reflection image received by the first light receiving unit after increasing the light intensity of the visible light projected by the second projecting unit.

Further features of the present invention will become apparent from the following description of exemplary embodiments with reference to the attached drawings.

DESCRIPTION OF THE EMBODIMENTS

First Embodiment

Figure 1:
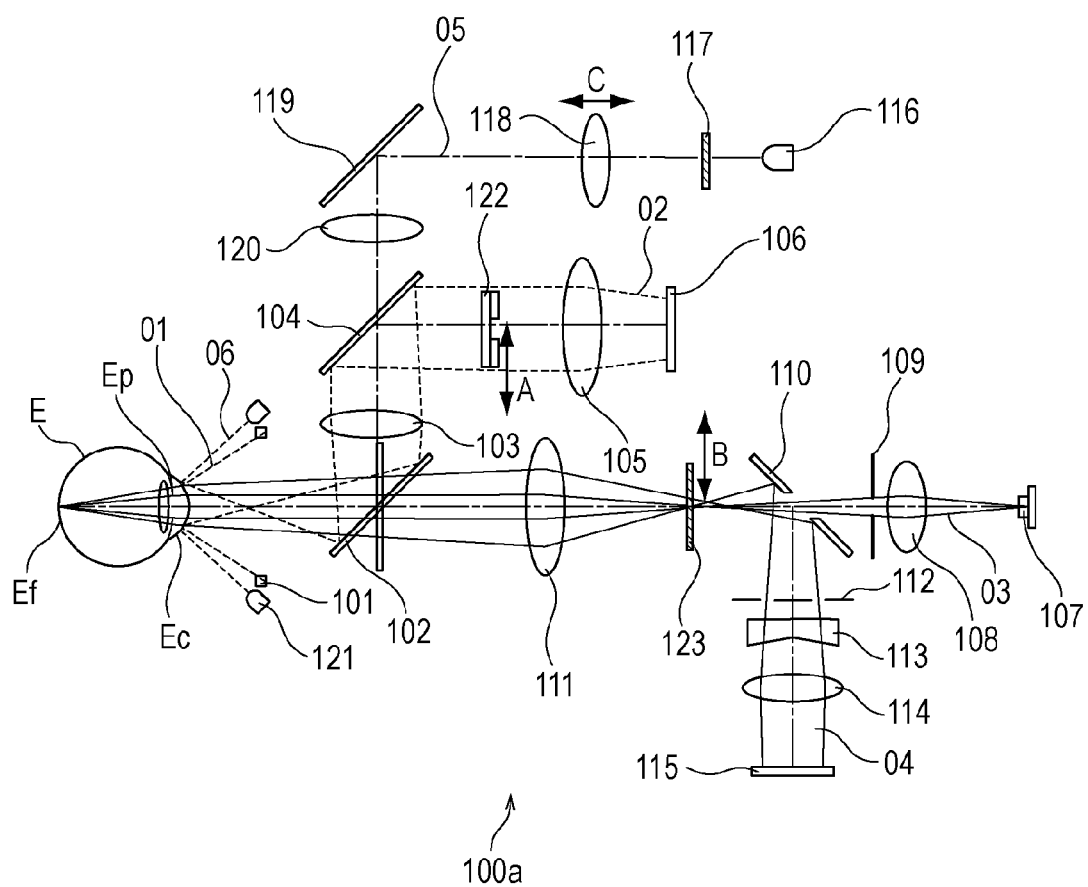
FIG. 1 is an arrangement diagram of an optical system according to a first embodiment and a second embodiment of the present invention.

A first embodiment of the present invention will be described in detail with reference to FIGS. 1 to 7. FIG. 1 is an optical system arrangement diagram of a measuring unit of an ocular characteristics measuring apparatus 100a according to the first embodiment of the present invention. An optical system of the ocular characteristics measuring apparatus 100a includes a cornea surface curvature measurement optical system, an ocular refractivity measurement optical system, a fixation target projection optical system, an alignment optical system, and an anterior eye portion observation optical system.

Cornea Surface Curvature Measurement Optical System

The cornea surface curvature measurement optical system includes a projection system and a light receiving system for the measurement of the cornea surface curvature.

An optical path 01 from a ring light source 101 to an eye to be examined E is the projection system for the measurement of the cornea surface curvature. The ring light source 101 emits light having a wavelength of 780 nm. This projection system is an example of a light flux cornea projecting unit (a first projecting unit). Here, consider an optical axis (a central axis) L0 of this optical path 01 as an optical axis of the ocular characteristics measuring apparatus 100a. The projection system which is an example of the light flux cornea projecting unit projects a light flux onto a cornea Ec of the eye to be examined E from the outside of the optical path 01 which is the central axis of the optical path of the ring light source 101.

An optical path 02 from the eye to be examined E to an image pickup element 106 is the light receiving system of the cornea surface curvature measurement optical system. This light receiving system is an example of a corneal reflection light flux receiving unit (a first light receiving unit). On the optical path 02, a dichroic mirror 102, a lens 103, a half mirror 104, a lens 105, and the image pickup element 106 are arranged in this order from the eye to be examined E side. The dichroic mirror 102 totally reflects visible light and partially reflects a light flux having a wavelength of 880 nm. An alignment prism diaphragm 122 is configured to be reciprocated in the direction of arrow A by an unillustrated diffuser plate insertion/removal solenoid. The alignment prism diaphragm 122 is disposed out of the optical path 02 when the measurement of the cornea surface curvature is performed.

The ring light source 101 and the image pickup element 106 are substantially conjugate with each other.

Projected light from the projection system (the light flux cornea projecting unit) including the ring light source 101 is reflected on a surface of the cornea Ec of the eye to be examined E. A corneal reflection light flux which is the reflected light flux passes through the optical path 02 and arrives at the image pickup element 106. At this time, an angle of reflection is changed depending on the curvature of the cornea Ec. For this reason, a ring image (a keratoring R) in accordance with the cornea surface curvature is projected on the image pickup element 106 as a corneal reflection image by the corneal reflection light flux for the calculation of the cornea surface curvature. The greater the cornea surface curvature, the larger the Keratoring R becomes. If the cornea Ec has a toric component, the Keratoring R is ellipse in shape. An image processing calculating unit 407 (described later) calculates the cornea surface curvature from the ring image which is an example of the corneal reflection image. That is, the image processing calculating unit corresponds to an example of a first calculating unit.

Although it had configuration by which ring light source 101 is applied to projection system which is an example of light flux cornea projecting unit here, it may not be ring light source 101. For example, a plurality of point light sources may be applied and the plurality of point light sources may draw a predetermined pattern. The pattern drawn by the ring light source 101 or the point light sources may have an arbitrary shape other than a circle.

Ocular Refractivity Measurement Optical System

The ocular refractivity measurement optical system includes a projection system and a light receiving system for the measurement of the ocular refractivity.

An optical path 03 from a light source 107 to the eye to be examined E is the projection system for the measurement of the ocular refractivity. The light source 107 emits light having a wavelength of 880 nm. This projection system is an example of a light flux eye fundus projecting unit (a third projecting unit). On the optical path 03 of this projection system, a lens 108, a diaphragm 109, a holed mirror 110, a lens 111, and a dichroic mirror 102 are arranged in this order from the light source 107 side. The diaphragm 109 is substantially conjugate with the pupil Ep of the eye to be examined E.

An optical path 04 from the eye to be examined E, reflected on the holed mirror 110 and arriving at the image pickup element 115 is the light receiving system for the measurement of the ocular refractivity. This light receiving system is an example of an eye fundus reflected light flux light receiving unit (a second light receiving unit). On the optical path 04 of this light receiving system, the dichroic mirror 102, the lens 111, a diffuser plate 123, the holed mirror 110, an ocular refractivity measurement diaphragm 112, a light flux separation prism 113, a lens 114, and an image pickup element 115 are arranged in this order from the eye to be examined E side.

The diffuser plate 123 is translucent and is movable by an unillustrated diffuser plate insertion/removal solenoid movable in the direction of arrow B. The diffuser plate 123 is disposed out of the optical path 04 when the measurement of the ocular refractivity is performed.

A light flux emitted from the light source 107 is condensed by the diaphragm 109, primarily forms an image before the lens 111 by the lens 108, passes through the lens 111 and the dichroic mirror 102, and is then projected onto the pupil center of the eye to be examined E. The light flux forms an image on an eye fundus Ef. Light is scattered by the eye fundus Ef and a part of the light enters the lens 111 again through the pupil Ep as the eye fundus reflected light flux. The eye fundus reflected light flux which has entered the lens 111 is reflected around the holed mirror 110 after passing through the lens 111. The reflected eye fundus reflected light flux undergoes pupil separation at the ocular refractivity measurement diaphragm 112 and the light flux separation prism 113 which are substantially conjugate with the pupil Ep of the eye to be examined E. The ocular refractivity measurement diaphragm 112 includes a ring shaped slit. For this reason, an eye fundus reflected light flux which has undergone pupil separation (an example of an eye fundus reflected light flux for the calculation of ocular refractivity) is projected onto a light-receiving surface of the image pickup element 115 as a ring image (an example of an eye fundus reflection image). If the eye to be examined E is an emmetropic eye, this ring image becomes a circle having a predetermined diameter. If the eye to be examined E is a short-sighted eye, the circle becomes smaller than that of the emmetropic eye. If the eye to be examined E is a long-sighted eye, the circle becomes larger than that of the emmetropic eye. If the eye to be examined E has astigmatism, the ring image becomes ellipse in shape. The image processing calculating unit 407 calculates ocular refractivity in accordance with the ring image (the eye fundus reflection image). In this case, the image processing calculating unit 407 (described later) functions as an example of an ocular refractivity calculating unit (a second calculating unit).

Fixation Target Projection Optical System

An optical path 05 from a visible light source for illuminating fixation target 116 to the eye to be examined E is the fixation target projection optical system. The fixation target projection optical system is an example of a fixation target projecting unit. On the optical path 05 of the fixation target projection optical system, a fixation target 117, a lens 118, a mirror 119, a lens 120, the half mirror 104, the lens 103, and the dichroic mirror 102 are arranged in this order from the visible light source for illuminating fixation target 116 side. The fixation target 117 is used to make the eye to be examined E hold fixation.

When the eye to be examined E is guided to hold fixation, a projection light flux emitted from the visible light source for illuminating fixation target 116 illuminates the fixation target 117 from the reverse side. The projection light flux is projected onto the eye fundus Ef of the eye to be examined E via the lens 118, the mirror 119, the lens 120, the half mirror 104, the lens 103, and the dichroic mirror 102. The lens 118 is movable in the direction of an optical axis (the direction of arrow C) by an unillustrated fixation holding guidance motor which performs diopter guidance control to implement a fogged state of the eye to be examined E.

In FIG. 1, a configuration in which the visible light source for illuminating fixation target 116 has a function to project visible light for the contraction of the pupil of the eye to be examined (which is an example of the visible light projecting unit (the second projecting unit)) is illustrated. Therefore, a visible light source for accelerating contraction of the pupil is not provided separately. However, a configuration in which a visible light source for accelerating contraction of the pupil is provided separately may also be used.

Alignment Optical System

The alignment optical system includes a projection system and a light receiving system for alignment.

The projection system for alignment is common to the projection system of the ocular refractivity measurement optical system. The projection system for alignment (the projection system for the measurement of the ocular refractivity) projects a light flux onto the cornea Ec of the eye to be examined E. When alignment is performed, the translucent diffuser plate 123 is disposed in the optical path 03 by an unillustrated diffuser plate insertion/removal solenoid. A position at which the diffuser plate 123 is inserted is a primary image formation position by the lens 108 of the light source 107 and is a focal position of the lens 111. The projection system for alignment is an example of a light flux cornea projecting unit for alignment.

The light receiving system for alignment is common to the light receiving system of the cornea surface curvature measurement optical system. However, when alignment is performed, the alignment prism diaphragm 122 is disposed in the optical path 02 by an unillustrated diffuser plate insertion/removal solenoid.

The light emitted from the light source 107 once forms an image on the diffuser plate 123 and becomes a secondary light source. The light which passed through the diffuser plate 123 (the light from the secondary light source) is projected as a thick collimated light flux toward the eye to be examined E from the lens 111. This collimated light flux is reflected on the cornea Ec of the eye to be examined E. The reflected light flux is split by the alignment prism diaphragm 122 and forms an image on the image pickup element 106 via the lens 105. A position of a bright spot of the image formed on the image pickup element 106 varies depending on the position of the eye to be examined E.

For this reason, a control unit 406 may align the eye to be examined E on the basis of the position of the bright spot.

Anterior Eye Portion Observation Optical System

The anterior eye portion observation optical system includes a projection system and a light receiving system for the observation of the anterior eye portion.

An optical path 06 from a light source 121 to the eye to be examined E is a projection system for the observation of the anterior eye portion. The light source 121 emits light having a wavelength of 780 nm. This projection system is an example of a pupil portion illumination unit. The light receiving system for the observation of the anterior eye portion is common to the light receiving system of the cornea surface curvature measurement optical system. The light reflected on the anterior eye portion (the pupil portion) of the eye to be examined E passes through the optical path 02 of the light receiving system of the cornea surface curvature measurement optical system and is projected onto the image pickup element 106. The image pickup element 106 photographs a projected anterior eye portion image (an example of a pupil portion image). The optical path 02 and the image pickup element 106 are examples of a pupil portion photographing unit. In this manner, an anterior eye portion image (an example of a pupil portion image) may be obtained. The image processing calculating unit 407 (an example of a pupil diameter calculating unit (a third calculating unit)) may extract an edge of the pupil and calculate a pupil diameter from the anterior eye portion image (the pupil portion image) at the time that the alignment is completed.

Principle of Generation of Keratoring and Ghost

Next, a principle of generation of the keratoring R and ghost R' obtained by the cornea surface curvature measurement optical system of FIG. 1 will be described with reference to FIGS. 2 and 3.

Figure 2:
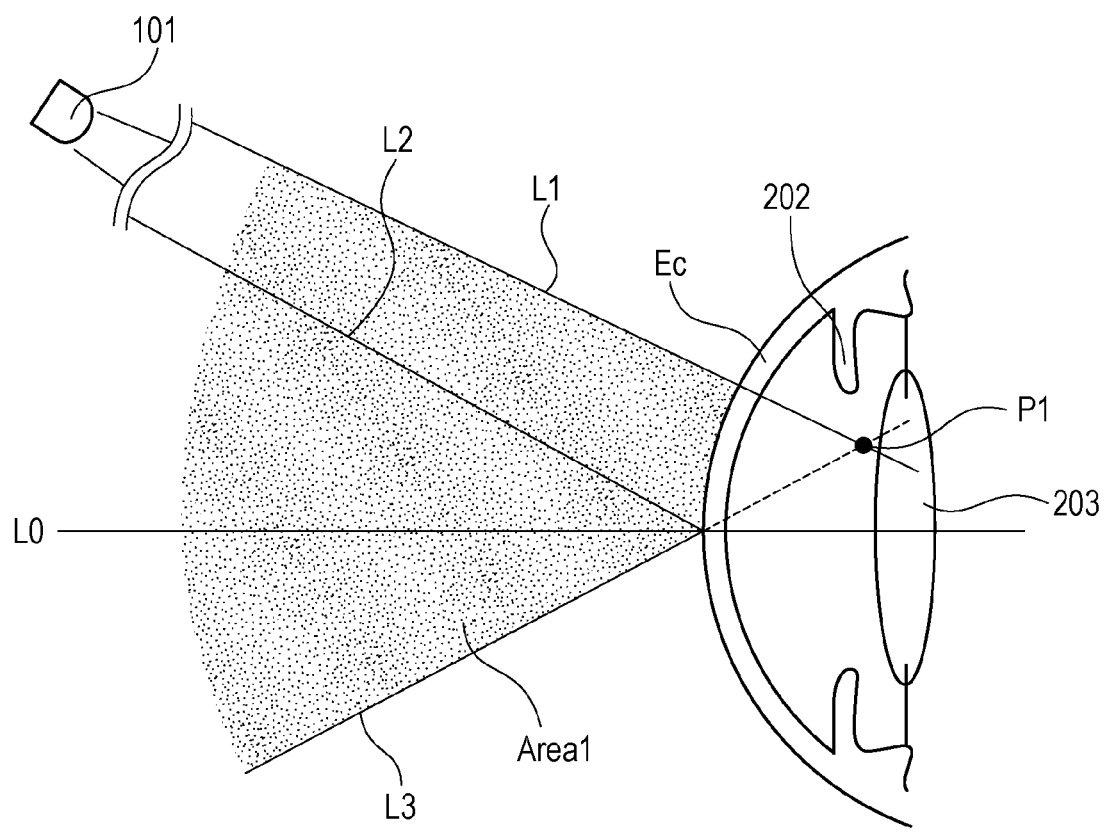
FIG. 2 is a diagram illustrating a principle of generation of keratoring.

FIG. 2 is a diagram illustrating the principle of generation of the keratoring R. In the drawing, line L1 is a line which perpendicularly crosses the cornea surface from the ring light source 101. Line L2 is a line which connects the ring light source 101 and the cornea center. Line L3 is a line which is optical-axially symmetrical to line L2. Measurement light emitted from the ring light source 101 is reflected on the surface of the cornea Ec. The reflected light forms a virtual image at a position P1 at which line L1 and line L3 cross each other. The keratoring R is obtained by photographing the reflected light flux which passes through an Area 1 (a dot region) with a focus on the virtual image position P1.

Figure 3:
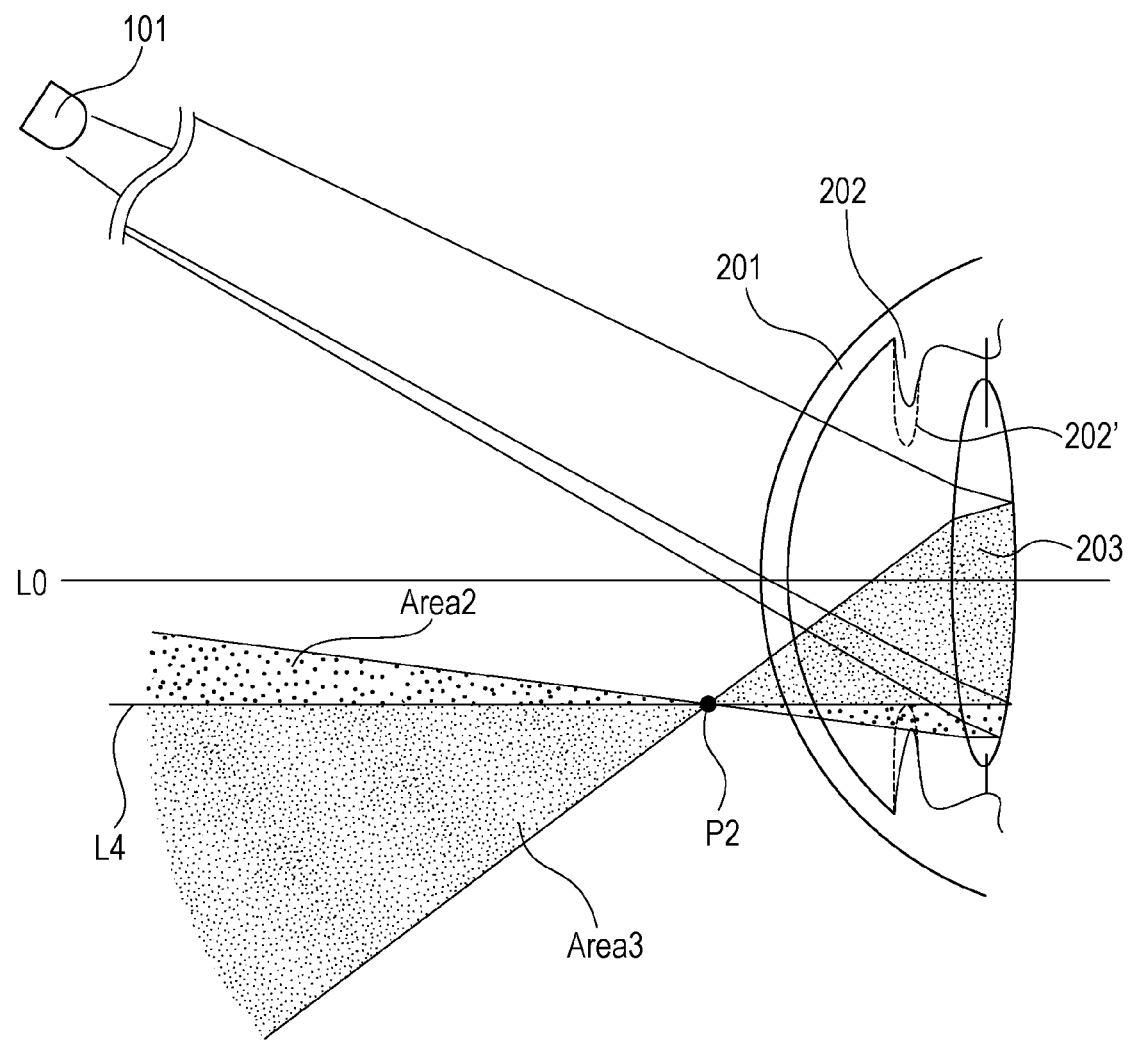
FIG. 3 is a diagram illustrating a principle of generation of ghost.

FIG. 3 is a diagram illustrating a principle of generation of the ghost R'. Measurement light emitted from the ring light source 101 forms an image at a position P2 when reflected on the back surface of an IOL 203. This real image is the ghost R'. In FIG. 3, optical paths of the measurement light in the case for of pupils of two sizes are illustrated. If the pupil diameter is large, as that of a pupil 202 illustrated by the solid line, the reflected light from the back surface of the IOL 203 forms an image at the position P2, and then returns to a main body of the ocular characteristics measuring apparatus 100*a* through Area 2 (an area with lower dot density) and Area 3 (an area with higher dot density). If this reflected light passes through the optical path 02 in FIG. 1 and is received by the image pickup element 106, the ghost R' is generated.

However, a part of the reflected light, especially a component which is emitted toward the outside of an optical axis L0 is blocked on the optical path or departs from the optical members (the dichroic mirror 102 and the lens 103 in FIG. 1). In FIG. 3, an area of the light flux which arrives at the image pickup element 106 is defined as Area 2 and an area of the light flux which does not arrive at the image pickup element 106 is defined as Area 3.

Here, a case in which the pupil 202 has been contracted as a pupil 202' illustrated by the dashed line will be considered. The ring light source 101 projects the light flux obliquely toward the cornea Ec from the outside of the optical axis L0. For this reason, the position P2 at which the image of the ghost R' is formed is separated from the optical axis L0. Therefore, the pupil 202 is contracted to about the size of a pupil 202' and thereby the light flux area Area 2 toward the optical axis L0 is blocked. As a result, the ghost R' is eliminated.

Line L4 which separates Area 2 and Area 3 is decided by the design of the optical members (the dichroic mirror 102 and the lens 103 in FIG. 1) and structural parts around them.

By downsizing the dichroic mirror 102 and the lens 103, line L4 may be made substantially parallel to the optical axis L0. In this case, the ghost R' may be eliminated by blocking the light flux on line L4 substantially parallel to the optical axis L0 at the position of the pupil 202'. In this case, a position of the top of the pupil is close to a line which is obtained by extending line L4 toward the pupil. Although refraction by the cornea Ec has occurred, since the distance between the cornea Ec and the pupil 202' is short, the top of the pupil and the line are close to each other. Therefore, the ghost R' may be eliminated by contracting the pupil to the position P2.

Influence of Ghost on Cornea Surface Curvature Measurement Accuracy

Figure 4A:
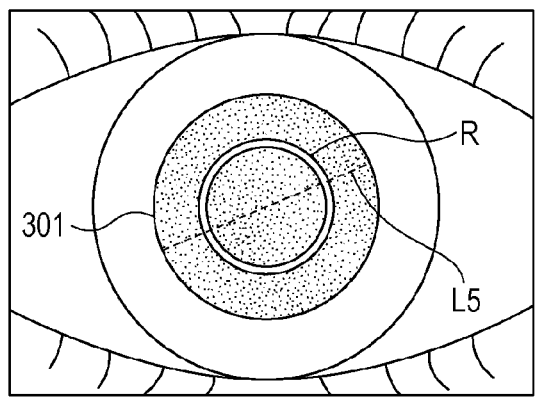
FIGS. 4A to 4D are diagrams illustrating how keratoring and ghost appear.
Figure 4B:
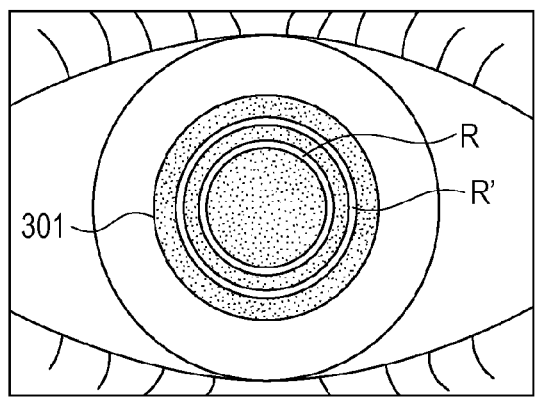
Figure 4C:
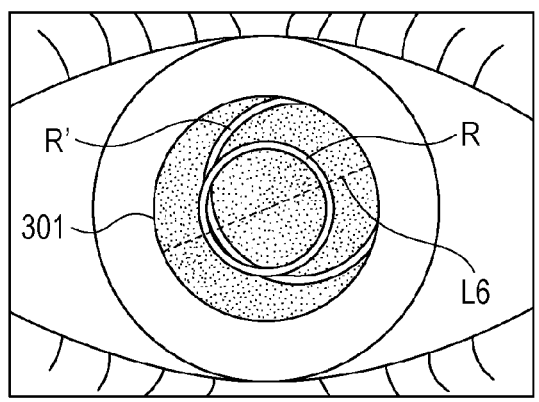

Next, with reference to FIGS. 4A to 4D and 5, an influence on cornea surface curvature measurement accuracy will be described. FIG. 4A illustrates the keratoring R for the measurement of the cornea surface curvature. FIGS. 4B and 4C each illustrates an image of an IOL eye in the measurement of the cornea surface curvature. In the images of IOL eye illustrated in FIGS. 4B and 4C, not only the keratoring R but the ghost R' due to IOL reflection have appeared. In an ideal case in which the IOL 203 is coaxial with the cornea center and is not inclined, and faces to the front, the ghost R' appears concentrically with the keratoring R as illustrated in FIG. 4B. However, actually, the position of the ghost R' is out of alignment with the keratoring R because the IOL is eccentrical with the cornea center, is inclined, and the like. FIG. 4C illustrates an example in which the position of the ghost R' is out of alignment with the center of the keratoring R. In FIG. 4C, a case in which line L4 in FIG. 3 is designed to be substantially parallel to the optical axis L0 is assumed. For this reason, an upper right portion of the ghost R' is eliminated about a pupil top 301.

Figure 4D:
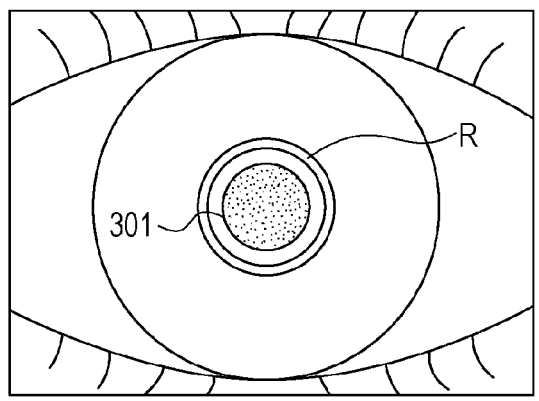
Figure 5:
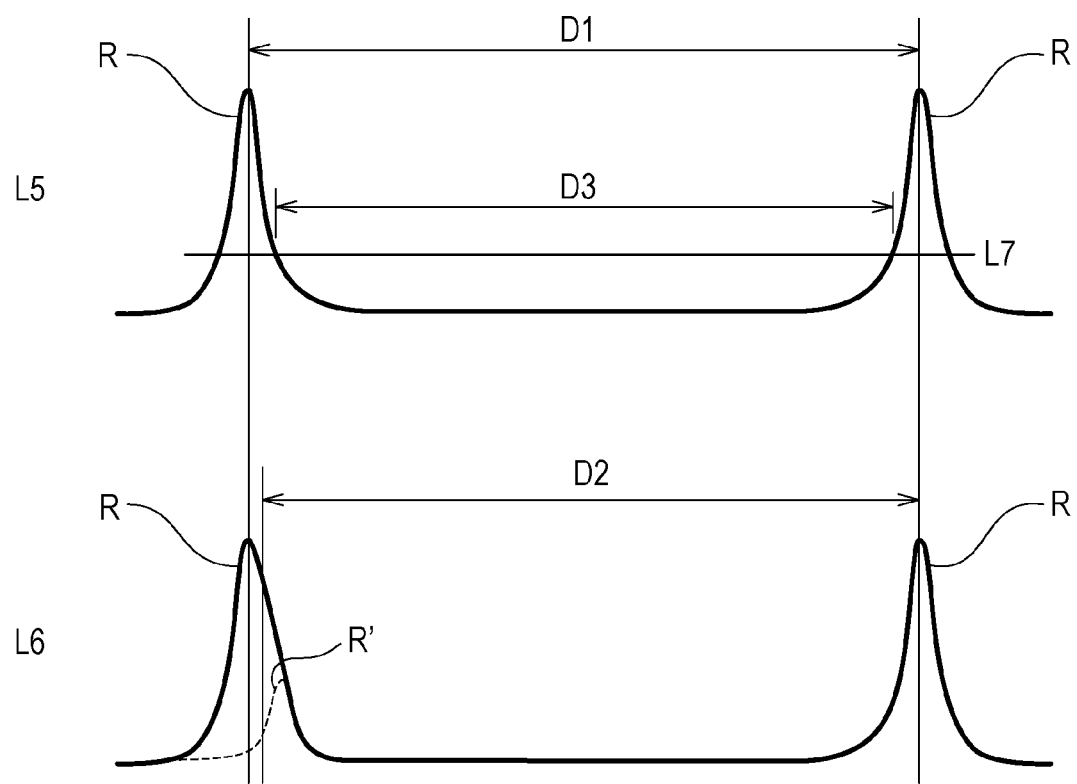
FIG. 5 is a diagram illustrating a luminance profile of a photographed image in which keratoring and ghost exist together.

FIG. 5 is a graph schematically illustrating an example of luminance distribution on line L5 of FIG. 4A and line L6 of FIG. 4C. Two peaks are formed by the keratoring R on line L5. The diameter of the ring image is calculated from a distance between centroids D1 of the peaks. On line L6, two peaks by the keratoring R and a peak by the ghost R' exist so as to partially overlap each other. For this reason, the center of gravity of the peak may be out of alignment by the ghost R'. Then, the distance between centroids becomes a distance between centroids D2 which is different from the original distance between centroids D1 and an error may be caused in the measurement of the cornea surface curvature. For example, in FIG. 4C, the diameter in the direction of line L6 becomes small and thus there is a possibility that an astigmatism component may be accidentally displayed by the ghost R'. Then, in the present embodiment, the ghost R' is eliminated by contraction of the pupil as illustrated in FIG. 4D. In this manner, a correct measurement of the cornea surface curvature may be performed.

Configuration and Operation of Ocular Characteristics Measuring Apparatus

Figure 6:
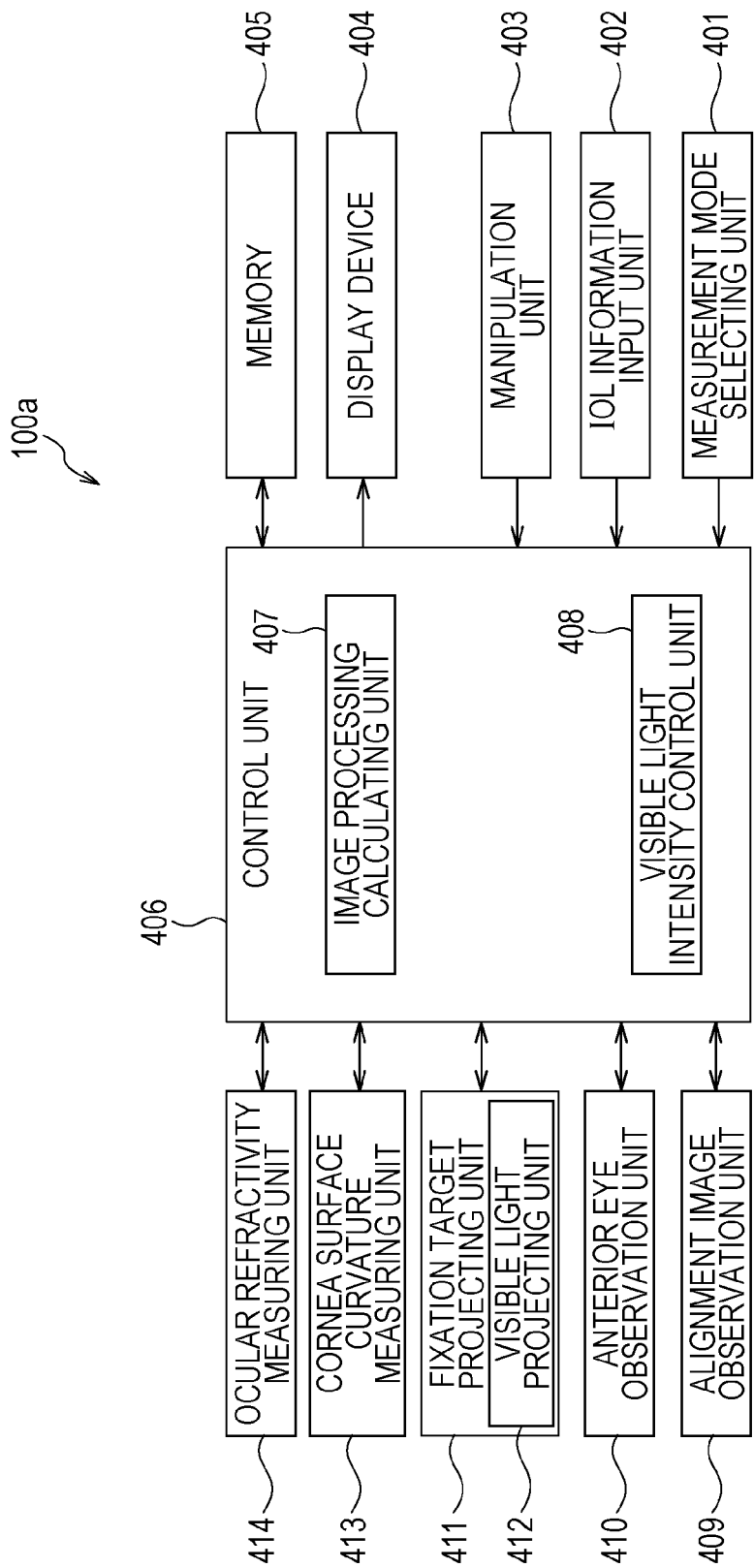
FIG. 6 is a system block diagram according to the first embodiment and the second embodiment of the present invention.

Next, a configuration and an operation of the ocular characteristics measuring apparatus 100a will be described using a system block diagram of FIG. 6 and a flowchart of FIG. 7.

An ocular refractivity measuring unit 414 includes the ocular refractivity measurement optical system described above. A cornea surface curvature measuring unit 413 includes the cornea surface curvature measurement optical system described above. A fixation target projecting unit 411 includes the fixation target projection optical system described above. The fixation target projecting unit 411 further includes a visible light projecting unit 412. The visible light projecting unit 412 projects visible light onto the eye to be examined E for the contraction of the pupil of the eye to be examined E. In the present embodiment, the visible light projecting unit 412 includes the visible light source for illuminating fixation target 116. However, a visible light source for the contraction of the pupil other than the visible light source for illuminating fixation target 116 may be provided. An anterior eye observation unit 410 includes the anterior eye portion observation optical system described above.

The control unit 406 controls each part of the ocular characteristics measuring apparatus 100a. The control unit 406 further includes the image processing calculating unit 407 and a visible light intensity control unit 408. The image processing calculating unit 407 performs a predetermined process using images obtained by each measuring unit, each observation unit, and the like (described later). The visible light intensity control unit 408 controls light intensity of visible light by the visible light projecting unit 412.

Memory 405 may store various data, such as calculation results of the image processing calculating unit 407 and images obtained by each measuring unit, each observation unit, and the like.

A display device 404 may display various messages, and images obtained by each measuring unit, each observation unit, and the like. Publicly known various display devices, such as a liquid crystal display device, may be used as the display device 404.

A manipulation unit 403 receives manipulation by a user. The control unit 406 controls each part in accordance with the content of the manipulation performed to the manipulation unit 403.

An IOL information input unit 402 is a portion manipulated by the user to register whether the eye to be examined E is an IOL eye. The control unit 406 registers, in the memory 405 or the like, information input through the IOL information input unit 402 (information about whether the eye to be examined E is an IOL eye). A measurement mode selection unit 401 is a portion manipulated by the used to select a measurement mode of the ocular characteristics measuring apparatus 100a. The control unit 406 operates in the measurement mode selected via the measurement mode selection unit 401.

First, the user performs a manipulation to select a measurement mode to the measurement mode selection unit 401 from among "continuous photographing of ocular refractivity measurement and cornea surface curvature measurement," "ocular refractivity measurement" and "cornea surface curvature measurement." The control unit 406 switches the measurement mode of the ocular characteristics measuring apparatus 100a to the measurement mode selected by the user.

Next, the ocular characteristics measuring apparatus 100a recognizes whether the eye to be examined E is an IOL eye. For example, if it is known in advance that the eye to be examined E is an IOL eye by the self-statement of a subject, the user may perform a manipulation to register (input) the eye to be examined E as the IOL eye from the IOL information input unit 402. In this case, the IOL information input unit 402 functions as an example of an intraocular lens information input unit. The control unit 406 recognizes whether the eye to be examined E is an IOL eye by determining the content registered (input) by the user via the IOL information input unit 402 (the intraocular lens information input unit). In this case, the control unit 406 functions as an example of an intraocular lens-inserted eye determination unit.

The user performs an alignment operation to the manipulation unit 403 while viewing, on the display device 404, an image obtained from an alignment image observation unit 409. The control unit 406 performs the alignment operation of the measuring unit in accordance with the manipulation to the manipulation unit 403 by the user. Alternatively, the image processing calculating unit 407 may analyze the image obtained from the alignment image observation unit 409, and the control unit 406 may automatically perform the alignment operation in accordance with the analysis result.

During or after this alignment operation, a preliminary photographing may be performed by the cornea surface curvature measuring unit 413. For example, in a configuration in which projection system for alignment is common to the projection system for the measurement of the ocular refractivity, the light flux emitted by the light source 107 is projected onto the cornea Ec of the eye to be examined E. Then the corneal reflection image is picked up by the image pickup element 106. The alignment optical system which includes the alignment image observation unit 409 has also detected a virtual image of the reflected light from the cornea Ec. For this reason, the ghost R' is generated by the reflected light from the back surface of the IOL 203 in the same manner as in the cornea surface curvature measurement. Then, it is also possible to automatically determine, by the image processing calculating unit 407, whether the eye to be examined E is an IOL eye by determining whether the ghost R' has been generated through an analysis of the image photographed by the image pickup element 106. In this case, the image processing calculating unit 407 functions as an example of the intraocular lens-inserted eye determination unit.

Therefore, alternatively, the alignment image observation unit 409 may determine whether the ghost R' has been generated during the alignment operation, and may determine whether the eye to be examined E is an IOL eye. In this case, the alignment image observation unit 409 functions as an example of the intraocular lens-inserted eye determination unit.

Figure 7:
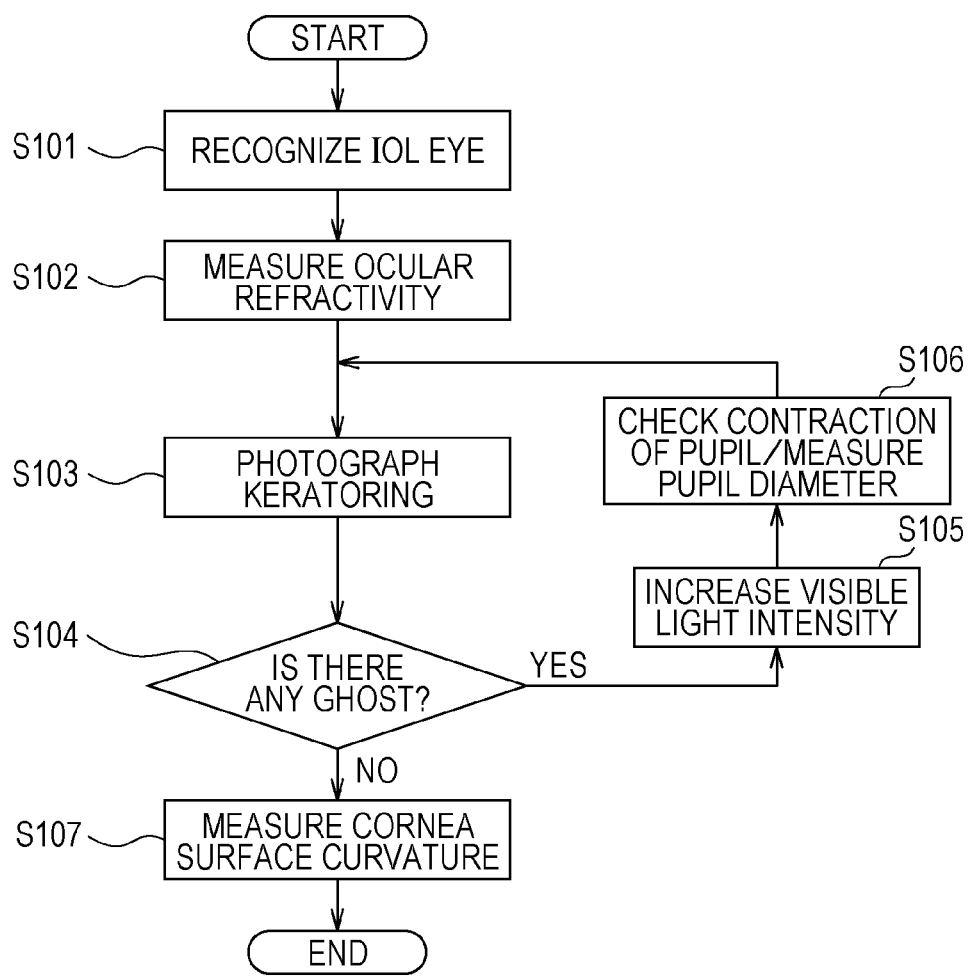
FIG. 7 is a flowchart according to the first embodiment of the present invention.

FIG. 7 is a flowchart in a case in which the eye to be examined E has been recognized as an IOL eye in the "continuous photographing of ocular refractivity measurement and cornea surface curvature measurement" mode.

In step S101, the control unit 406 determines whether the eye to be examined E is an IOL eye as described above.

In step S102, the control unit 406 starts the ocular refractivity measuring unit 414 to perform ocular refractivity measurement. First, the image pickup element 115 receives the ring image (an example of the eye fundus reflection image). The image pickup element 115 picks up the ring image. The image processing calculating unit 407 (an example of the ocular refractivity calculating unit) calculates ocular refractivity in accordance with the picked ring image.

In the present embodiment, the eye to be examined E is contracted in order to eliminate the ghost R' resulting from the IOL 203 at the time of the cornea surface curvature measurement. However, when the pupil diameter is reduced, there is a possibility that the measurement of the ocular refractivity becomes impossible. That is, if the pupil is excessively small, the reflected light does not arrive at the slit of the ocular refractivity measurement diaphragm 112 in FIG. 1 anymore, and the ring image no longer be obtained. For this reason, it is better to perform the ocular refractivity measurement before the contraction of the pupil. Before the recognition of the IOL eye (S101) is performed, the measuring unit is started in accordance with a normal measurement flowchart. For example, typically, in consideration of the fatigue due to eyelid opening of the eye to be examined E, the measurement of the cornea surface curvature in which an eyelid of the eye to be examined E needs to be opened wider may be performed before the measurement of the ocular refractivity. In this case, when "continuous photographing of ocular refractivity measurement and cornea surface curvature measurement" mode is selected, the cornea surface curvature measuring unit 413 becomes an active condition. Then, the control unit 406 performs an operation to switch the ocular refractivity measuring unit 414 to an active condition by recognizing the IOL eye. If an operation to select "cornea surface curvature measurement" mode is performed to the measurement mode selection unit 401, the control unit 406 displays an alert of "if measurement of ocular refractivity is needed, do it first" and the like on the display device 404. In this manner, the control unit 406 performs an operation to encourage the user to perform the measurement in the order of "ocular refractivity measurement" and then "cornea surface curvature measurement."

When the measurement of the ocular refractivity is completed, the control unit 406 stores the measurement value in the memory 405. The process proceeds to step S103.

In step S103, the control unit 406 starts the cornea surface curvature measuring unit 413. The control unit 406 makes the cornea surface curvature measuring unit 413 photograph the keratoring R.

In step S104, the image processing calculating unit 407 analyzes an image of the photographed keratoring R and determines whether any ghost R' exists. If the ghost R' exists, the image processing calculating unit 407 determines to increase the light intensity of the visible light by the visible light projecting unit 412. In this manner, in the present embodiment, the image processing calculating unit 407 is an example of an visible light intensity increase determination unit which determines whether the light intensity of the visible light by the visible light projecting unit 412 is to be increased. If the ghost R' exists, the process proceeds to step S105.

In step S105, the visible light intensity control unit 408 causes the projected light intensity of the visible light by the visible light projecting unit 412 to be increased (changed) and encourages contraction of the pupil of the eye to be examined E. In this manner, in the present embodiment, the image processing calculating unit 407 functions as an example of the visible light intensity control unit which changes the light intensity of the visible light projecting unit 412.

In the present embodiment, the visible light source for illuminating fixation target 116 in the fixation target projecting unit 411 functions as the visible light projecting unit 412. The light intensity of the visible light projecting unit 412 is uniquely determined to light intensity suitable for a typical eye to be examined which is not an IOL eye to hold fixation from the operation start of the ocular characteristics measuring apparatus 100a until the completion of the alignment. The visible light intensity control unit 408 instructs the visible light projecting unit 412 to change the light intensity to be higher than the light intensity set for an eye to be examined which is not an IOL eye (the light intensity set for alignment). When the visible light projecting unit 412 has changed the light intensity to be higher than the light intensity set for an eye to be examined which is not an IOL eye, the visible light intensity control unit 408 may display an alert of "light intensity of fixation target lamp is set high to encourage contraction of pupil" and the like on the display device 404. With this configuration, it may be avoided that the user causes the ocular characteristics measuring apparatus 100a to perform other operations by mistake while waiting for the contraction of the pupil. In consideration of the time required for the contraction of the pupil, the process proceeds to step S106 after predetermined time elapses.

In step S106, the image processing calculating unit 407 analyzes an image obtained from the anterior eye observation unit 410 and calculates the pupil diameter. The image processing calculating unit 407 then confirms that contraction of the pupil is being performed. If it is confirmed that the contraction of the pupil is performed, the process again proceeds to step S103.

In this manner, the operations and processes of S103 to S105 are repeated until the ghost R' is eliminated.

When it is confirmed in S104 that the ghost R' has been eliminated, the process proceeds to step S107.

In step S107, the control unit 406 performs the measurement of the cornea surface curvature in accordance with the manipulation of the user. As described above, the image pickup element 106 obtains the ring image (the keratoring R) in accordance with the cornea surface curvature as the corneal reflection image for the calculation of the cornea surface curvature by the corneal reflection light flux. The greater the cornea surface curvature, the larger the Keratoring R becomes. If the cornea Ec has a toric component, the Keratoring R is ellipse in shape. Then, the image processing calculating unit 407 calculates the cornea surface curvature from the ring image. The control unit 406 stores the measurement value in the memory 405. At the time of the measurement of the cornea surface curvature, the image processing calculating unit 407 may calculate the cornea surface curvature from the keratoring R photographed in step S103.

By following the operation flow described above, the influence of the ghost R' caused by the IOL 203 at the time of the measurement of the cornea surface curvature may be avoided. For this reason, correct measurement of the cornea surface curvature may be performed.

Second Embodiment

Subsequently, a second embodiment of the present invention will be described. Configurations common to those of the first embodiment will be denoted by the same reference numerals as those of the first embodiment and description thereof will be omitted.

Figure 8A:
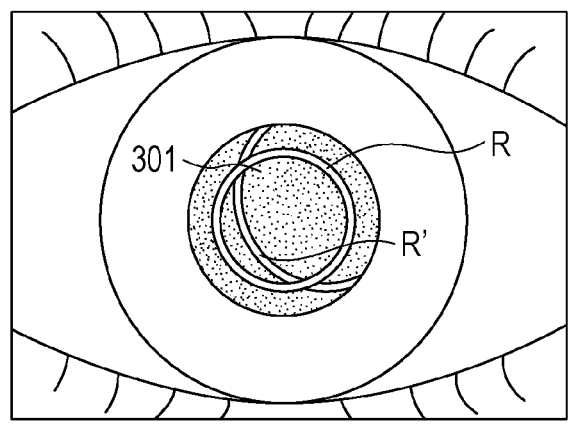
FIGS. 8A and 8B are diagrams illustrating a state in which ghost has appeared greatly out of alignment with keratoring.
Figure 8B:
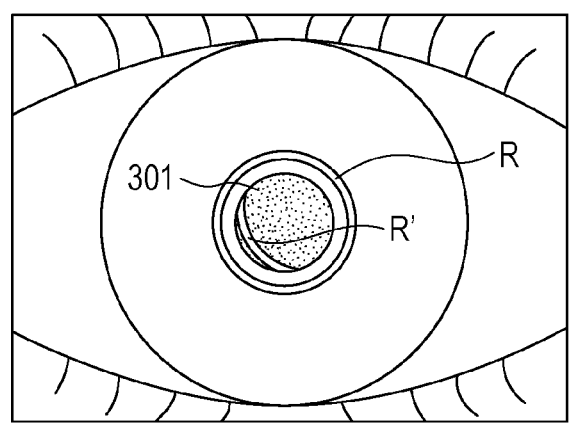

In the first embodiment, it is checked whether the ghost R' has been generated in the photographed image in the measurement of the cornea surface curvature and the visible light intensity is increased (changed) in accordance with the result. In this configuration, it is difficult to know to what extent the light intensity should be increased for the elimination of the ghost R'. For this reason, there is a possibility that the eye to be examined E undergoes stress by being exposed to unnecessarily intensive visible light. Then, in the second embodiment, the size of the pupil diameter is used as an index, whereby correct measurement of the cornea surface curvature may be performed without increasing the visible light intensity more than necessary. As described above, if line L4 in FIG. 3 is substantially parallel to the optical axis L0, the ghost R' is hidden just on the boundary of the pupil. That is, it is possible to predict whether the ghost R' exists using the pupil diameter as an index. Further, as illustrated in FIG. 8A, for example, if the IOL 203 is inclined greatly or is eccentrical inside the eye to be examined E, the ghost R' becomes greatly out of alignment with the keratoring R. In this case, it is necessary to illuminate extremely intensive visible light to completely eliminate the ghost R'. If the ghost R' exists near the pupil center, it is not possible to completely eliminate the ghost R'. However, as illustrated in FIG. 8B, by decreasing the size of the pupil diameter smaller than the inner diameter of the keratoring R, it is possible to separate the keratoring R and the ghost R' so that the keratoring R and the ghost R' do not overlap each other. With such separation, it is possible to eliminate the influence of the ghost R' easily by image processing and to correctly measure the cornea surface curvature. As described above, by increasing the visible light intensity until the pupil diameter becomes smaller than the inside of the keratoring R and then keeping the light intensity so as not to increase anymore, an unnecessary increase in the visible light intensity may be avoided.

Operation of Ocular Characteristics Measuring Apparatus

Figure 9:
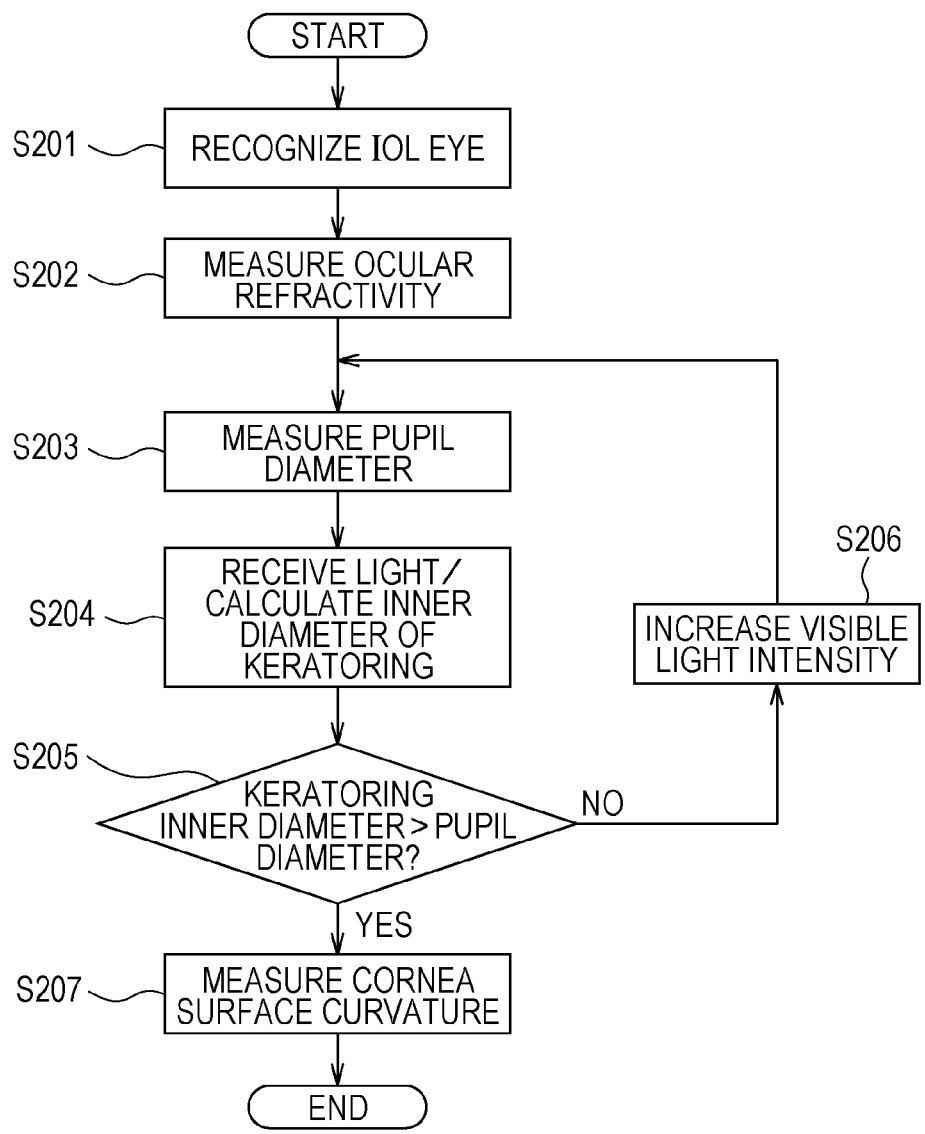
FIG. 9 is a flowchart according to the second embodiment of the present invention.

FIG. 9 is a flowchart illustrating an operation of the ocular characteristics measuring apparatus 100a in the second embodiment. After the ocular characteristics measuring apparatus 100a starts operation, recognition of the IOL eye (step S201) and measurement of ocular refractivity (step S202) are respectively the same as S101 and S102 of FIG. 7 in the first embodiment.

In step S203, the image processing calculating unit 407 analyzes an image obtained from the anterior eye observation unit 410 and calculates the pupil diameter so as to confirm that contraction of the pupil is being performed.

In step S204, the cornea surface curvature measuring unit 413 performs preliminary photographing to obtain a keratoring image. The image processing calculating unit 407 then analyzes the obtained keratoring image and calculates the inner diameter of the keratoring R.

In step S205, the image processing calculating unit 407 compares the obtained pupil diameter and the inner diameter of the keratoring R. A calculating method of the inner diameter of the keratoring R is as follows. As illustrated in FIG. 5, the image processing calculating unit 407 recognizes, as a ring image, luminance of threshold L7 or greater which is set in advance, of the two peaks by the ring image. Then the image processing calculating unit 407 may obtain a distance D3 at the position on line L7 inside of the two peaks as the inner diameter of the keratoring R. If the inner diameter of the keratoring R is smaller than the pupil diameter, the process proceeds to step S206.

In step S206, the visible light intensity control unit 408 causes the projected light intensity of the visible light by the visible light projecting unit 412 to be increased and encourages contraction of the pupil. In consideration of the time required for the contraction of the pupil, the process returns to step S203 after predetermined time elapses. After the process returns to step S203, the measurement of the pupil diameter (S203) is performed again. In step S205, the process flow of steps S203 to S206 is repeated until the pupil diameter becomes smaller than the inner diameter of the keratoring R.

In S205, when the pupil diameter becomes smaller than the inner diameter of the keratoring R, the process proceeds to step S207.

In step S207, the control unit 406 performs the measurement of the cornea surface curvature in accordance with the manipulation of the user. The control unit 406 stores the measurement value in the memory 405.

In this manner, the pupil diameter is made smaller than the inner diameter of the keratoring R. Thus, the ghost R' may be eliminated or the ghost R' may be clearly separated from the keratoring R. Therefore, correct measurement of the cornea surface curvature may be performed.

Third Embodiment

An ocular characteristics measuring apparatus 100c according to a third embodiment has a cornea thickness measuring function in addition to the function of measuring the cornea surface curvature and the ocular refractivity.

Figure 10:
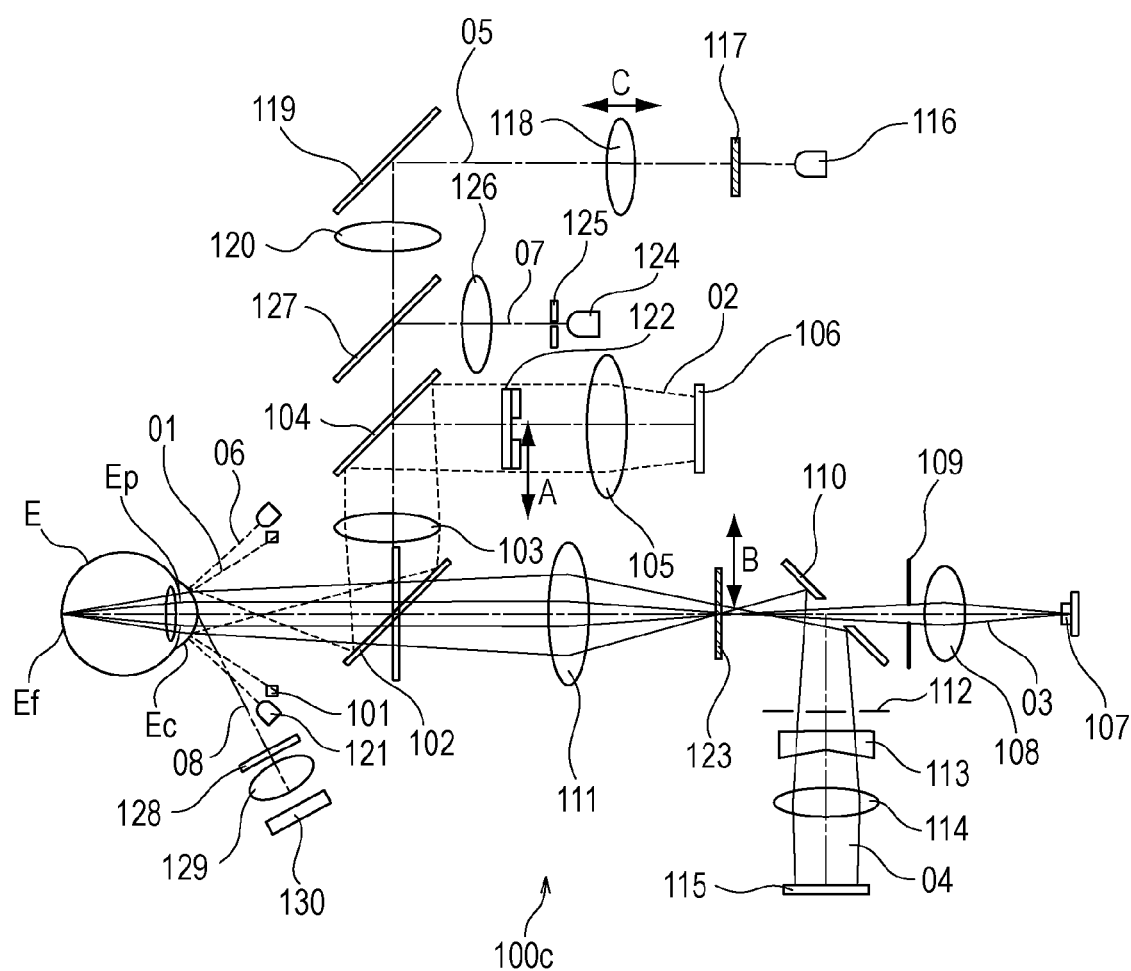
FIG. 10 is an arrangement diagram of an optical system according to a third embodiment of the present invention.

FIG. 10 is an optical system arrangement diagram of a measuring unit of an ocular characteristics measuring apparatus 100c according to the third embodiment of the present invention. An optical system of the ocular characteristics measuring apparatus 100c includes a cornea thickness measurement optical system, a cornea surface curvature measurement optical system, an ocular refractivity measurement optical system, a fixation target projection optical system, an alignment optical system, and an anterior eye portion observation optical system. The optical system of the third embodiment is the same as the optical system of the first embodiment illustrated in FIG. 1 to which the cornea thickness measurement optical system is added, and other configurations are the same as those of the first embodiment. Configurations common to those of the first embodiment or the second embodiment will be denoted by the same reference numerals as those of the first embodiment or the second embodiment and description thereof will be omitted.

Cornea Thickness Measurement Optical System

The cornea thickness measurement optical system includes a projection system and a light receiving system for the measurement of the cornea thickness.

An optical path 07 from a light source 124 to the eye to be examined E is the projection system for the measurement of the cornea thickness. The light source 124 emits light having a wavelength of 450 nm. This projection system is an example of a slit light projecting unit and projects slit light onto the cornea Ec of the eye to be examined E. On the optical path 07 of the projection system (the slit light projecting unit), a slit plate 125, a lens 126, a half mirror 127, a half mirror 104, a lens 103, and a dichroic mirror 102 are arranged in this order from the light source 124 side. This projection system projects visible light onto the eye to be examined E to make the eye to be examined E contract. That is, in the present embodiment, this projection system also has a function as a visible light projecting unit.

An optical path 08 from the eye to be examined E to an image pickup element 130 is a light receiving system for the measurement of the cornea thickness. This light receiving system is an example of a cornea scattered light flux light receiving unit. On the optical path 08 of the light receiving system (the cornea scattered light flux light receiving unit), a filter 128, a lens 129, and the image pickup element 130 are arranged in this order from the eye to be examined E side. The filter 128 transmits light having a cornea scattered light wavelength region from the light source 124.

The optical path 07 which is the projection optical system and the optical path 08 which is the light receiving system cross at the vertex of the cornea Ec. The slit plate 125, the cornea Ec and the image pickup element 130 are substantially conjugate with one another.

The light source 124 illuminates the slit plate 125. An image of the slit plate 125 (the slit light) forms an image on the cornea Ec by the lens 126 and the lens 103. The projected light (the slit light) is scattered while passing through the cornea Ec and forms a cornea scattered light flux. This cornea scattered light flux is an example of a cornea scattered light flux for the calculation of the cornea thickness.

Excessive light of the cornea scattered light flux is removed by the filter 128. Then, the cornea scattered light flux forms an image on the image pickup element 130 by the lens 129. The cornea scattered light flux imaged on the image pickup element 130 is an example of a cornea scattering image. In this manner, a cornea cross-sectional image is obtained in the image pickup element 130 and the image processing calculating unit 407 (an example of a cornea thickness calculating unit (a fourth calculating unit)) may calculate the cornea thickness from the width of the cornea cross-sectional image.

Configuration and Operation of Ocular Characteristics Measuring Apparatus

Next, a configuration and an operation of the ocular characteristics measuring apparatus 100c according to the third embodiment will be described using a system block diagram of FIG. 11 and a flowchart of FIG. 12.

Configurations Common to Those of the First Embodiment Will be Denoted by the Same Reference Numerals and Description Thereof Will be Omitted.

Figure 11:
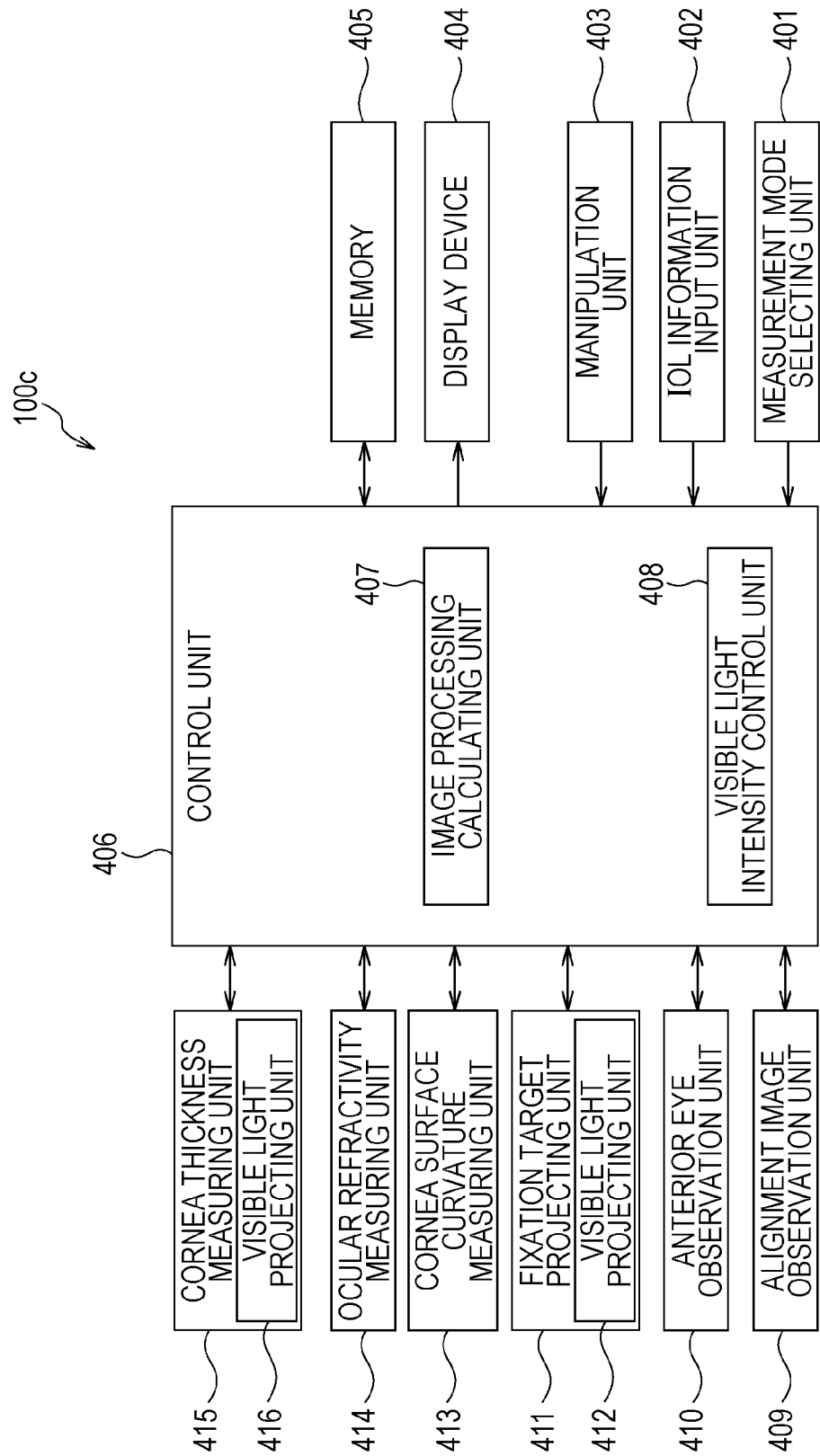
FIG. 11 is a system block diagram according to the third embodiment of the present invention.

As illustrated in FIG. 11, the ocular characteristics measuring apparatus 100c includes a cornea thickness measuring unit 415. The cornea thickness measuring unit 415 includes the cornea thickness measurement optical system described above. The cornea thickness measuring unit 415 further includes a visible light projecting unit 416. As described above, a projection system of the cornea thickness measurement optical system also has a function as an example of the visible light projecting unit. A configuration common to that of the first embodiment may be used on the rest of the points.

Figure 12:
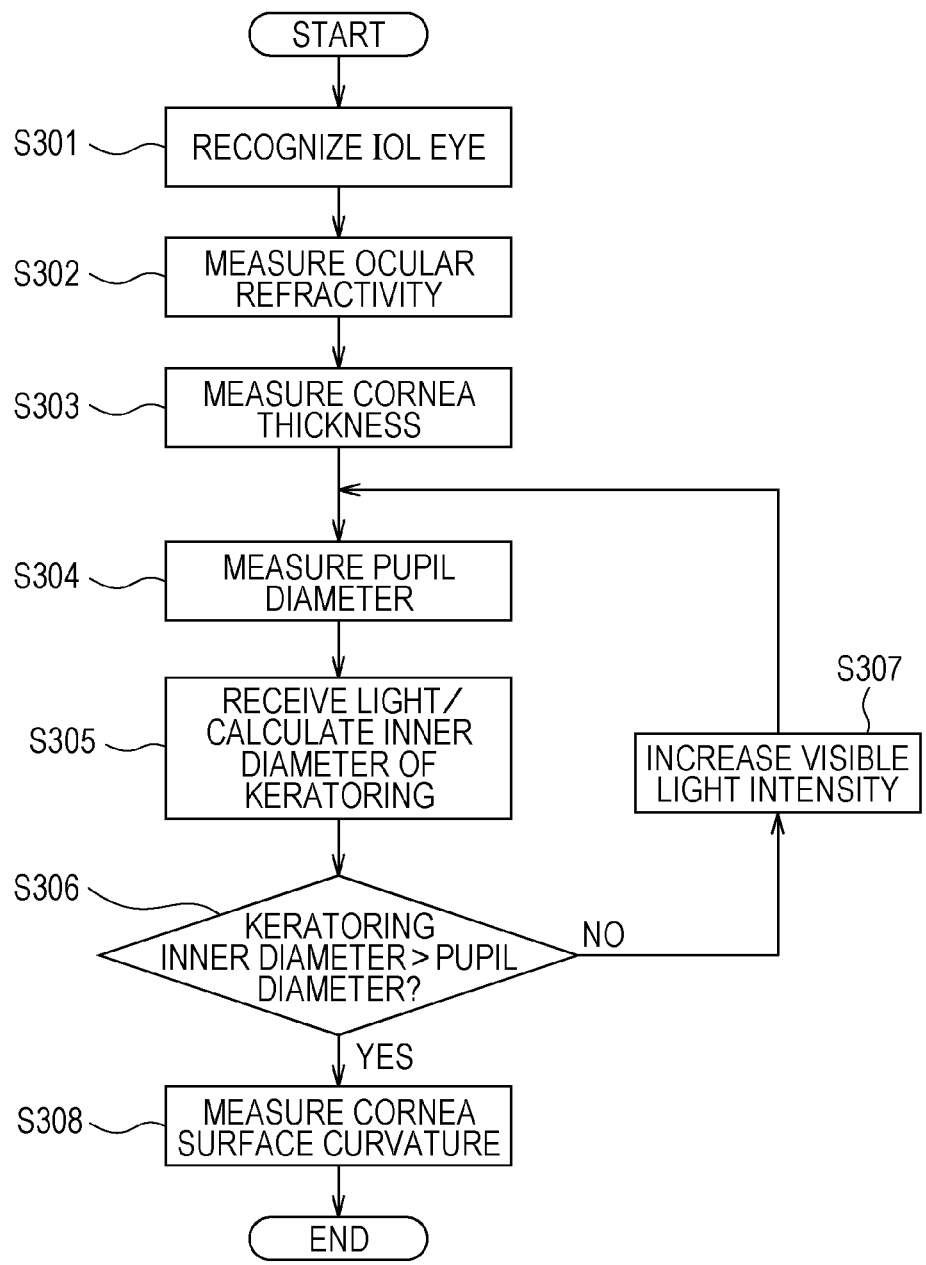
FIG. 12 is a flowchart according to the third embodiment of the present invention.

The flowchart of FIG. 12 illustrates a flow of an operation in a case in which the eye to be examined E has been recognized as an IOL eye in "continuous photographing of ocular refractivity measurement, cornea surface curvature measurement, and cornea thickness measurement" mode. After the ocular characteristics measuring apparatus 100c starts operation, recognition of the IOL eye in step S301 and measurement of the ocular refractivity in step S302 are respectively the same as step S101 and S102 of FIG. 7 of the first embodiment.

In step S303, the cornea thickness measuring unit 415 performs the measurement of cornea thickness. As described above, the image pickup element 130 picks a cornea scattering image by the cornea scattered light flux. In this manner, the cornea cross-sectional image is obtained. The image processing calculating unit 407 calculates cornea thickness from the cornea cross-sectional image. In this manner, in the present embodiment, the image processing calculating unit 407 functions as an example of the cornea thickness calculating unit.

Light of a visible light region of a wavelength of 450 nm is used for the measurement of cornea thickness. For this reason, there is a case in which the eye to be examined E is contracted due to dazzling at the time of the measurement. Therefore, if the pupil has been contracted and the ghost R' has been eliminated at the time of the measurement of the cornea thickness, time and effort to increase the visible light intensity and make the pupil contract may be saved. Then, in the third embodiment, the measurement of the cornea thickness is performed before the measurement of the cornea surface curvature. Subsequent operation flows (steps S304 to S308) are the same as steps S203 to S207 of the second embodiment.

If it is determined that the pupil diameter is equal to or smaller than the inner diameter of the keratoring R by the measurement of the cornea thickness, the process proceeds directly to the measurement of the cornea surface curvature.

If the pupil diameter is larger than the inner diameter of the keratoring R, the visible light intensity is increased. After it is confirmed that the pupil diameter has become smaller than the inner diameter of the keratoring R, the process proceeds to the measurement of the cornea surface curvature.

In the first embodiment and the second embodiment, projection of the visible light is performed by the visible light projecting unit 412 (the visible light source for illuminating fixation target 116) in the fixation target projecting unit 411. In the third embodiment, projection of the visible light may be performed in the same manner as in the first embodiment and the second embodiment. It is also possible to accelerate the contraction of the pupil by projection of visible light from a visible light projecting unit 416 (a light source 124) provided in the cornea thickness measuring unit 415. That is, the visible light projecting unit 416 which is an example of a slit light projecting unit may function as an example of the visible light projecting unit.

In the third embodiment, on the basis of the operation of the second embodiment, an operation flow in which the cornea thickness measuring function is included has been described; however, the operation on the basis of the first embodiment may be performed. Also in this case, the measurement of the cornea thickness is performed immediately after the measurement of the ocular refractivity.

By following the operation flow described above, efficient measurement may be performed in the case of an ocular characteristics measuring apparatus which has a cornea thickness measuring function.

Common Configuration of Ocular Characteristics Measuring Apparatus

Here, hardware configurations of the ocular characteristics measuring apparatuses 100*a* and 100*c* according to each embodiment will be described briefly. For each component illustrated in FIGS. 6 and 11, a PC, a microcomputer control apparatus, a logic control circuit, and the like are applied and specific configuration is not limited. Each component may be implemented by a computer which executes programs. In this case, ocular characteristics measuring apparatus 100*a* and 100*c* has computer, and computer program for controlling ocular characteristics measuring apparatus 100*a* and 100*c* is stored in various storage media, such as ROM and HDD, computer-readable. When a CPU of the computer reads and executes the computer programs, the computer functions as each component illustrated in FIGS. 6 and 11 and the processes illustrated in FIGS. 7, 9 and 12 are performed.

An embodiment of the present invention is implemented also by performing the following process. That is, a computer-readable program (software) which implements the functions of the embodiments described above is supplied to a system or a device via a network or various recording mediums, and a computer (or CPU, MPU and the like) of the system or the device reads and executes the program. In this case, the program and the recording medium on which the program is stored constitute the present invention.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™, a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-104247, filed May 16, 2013 which is hereby incorporated by reference herein in its entirety.

What is claimed is:

1. An ocular characteristics measuring apparatus, comprising:
    a first projecting unit configured to project a light flux onto a cornea of an eye to be examined from the outside of a central axis of an optical path, the eye having an intraocular lens inserted therein;
    a light receiving unit configured to receive a corneal reflection light flux and an intraocular lens reflection light flux by the first projecting unit;
    a calculating unit configured to calculate a cornea surface curvature in accordance with an corneal reflection image received from the light receiving unit;
    a second projecting unit configured to project visible light onto the eye to be examined; and
    a control unit configured to
        change a light intensity of the visible light projected by the second projecting unit,
        increase the light intensity of the visible light projected by the second projecting unit until the intraocular lens reflection light flux is not received by the light receiving unit or until the corneal reflection image does not overlap with an intraocular lens reflection image received from the light receiving unit.

2. The ocular characteristics measuring apparatus according to claim 1, further comprising:
    a third projecting unit configured to project a light flux onto an eye fundus of the eye to be examined;
    a second light receiving unit configured to receive an eye fundus reflected light flux from the third projecting unit; and
    a second calculating unit configured to calculate ocular refractivity in accordance with an eye fundus reflection image received by the second light receiving unit,
    wherein, before the first light receiving unit receives a corneal reflection light flux for the calculation of the cornea surface curvature, the eye fundus reflected light flux light receiving unit receives the eye fundus reflected light flux for the calculation of the ocular refractivity.

3. The ocular characteristics measuring apparatus according to claim 1, further comprising:
    a pupil portion illumination unit configured to illuminate a pupil portion of the eye to be examined;

a pupil portion photographing unit configured to photograph a pupil portion image illuminated by the pupil portion illumination unit;

a third calculating unit configured to calculate a pupil diameter in accordance with the pupil portion image; and a determination unit configured to determine whether the light intensity of the second projecting unit should be increased to be higher than light intensity set at the time of alignment in accordance with the size of the corneal reflection image and the pupil diameter calculated by the third calculating unit.

4. The ocular characteristics measuring apparatus according to claim 1, wherein the second projecting unit is a fixation target projecting unit to project a fixation target onto the eye to be examined.

5. The ocular characteristics measuring apparatus according to claim 4, further comprising:

a slit light projecting unit configured to project slit light onto a cornea of the eye to be examined;

a third light receiving unit configured to receive a cornea scattered light flux from the slit light projecting unit; and a fourth calculating unit configured to calculate a cornea thickness in accordance with a cornea scattering image received by the third light receiving unit, wherein, before the first light receiving unit receives a corneal reflection light flux for the calculation of the cornea surface curvature, the third light receiving unit receives the cornea scattered light flux for the calculation of the cornea thickness.

6. The ocular characteristics measuring apparatus according to claim 1, further comprising:

a slit light projecting unit configured to project slit light onto a cornea of the eye to be examined;

a third light receiving unit configured to receive a cornea scattered light flux from the slit light projecting unit; and a fourth calculating unit configured to calculate a cornea thickness in accordance with a cornea scattering image received by the third light receiving unit, wherein the visible light projecting unit is the slit light projecting unit.

7. The ocular characteristics measuring apparatus according to claim 1, further comprising an intraocular lens information input unit configured to input that the intraocular lens is inserted in the eye to be examined.

8. The ocular characteristics measuring apparatus according to claim 1, further comprising an intraocular lens-inserted eye determination unit configured to determine whether the intraocular lens is inserted in the eye to be examined in accordance with the corneal reflection image received by the first light receiving unit.

9. The ocular characteristics measuring apparatus according to claim 1, further comprising:

a first projecting unit for alignment configured to project a light flux onto a cornea of the eye to be examined; and another intraocular lens-inserted eye determination unit configured to determine whether the intraocular lens is inserted in the eye to be examined in accordance with a corneal reflection image formed by the light flux cornea projecting unit for the alignment received by the first light receiving unit.

10. The ocular characteristics measuring apparatus according to claim 1, wherein the calculating unit calculates the cornea surface curvature in accordance with the corneal reflection image received from the light receiving unit after increasing the light intensity of the visible light projected by the second projecting unit.

11. The ocular characteristics measuring apparatus according to claim 1, wherein the first projecting unit comprises a ring light source which emits infrared light.

12. The ocular characteristics measuring apparatus according to claim 11, wherein the light receiving unit comprises an image pickup element which is substantially conjugate with the ring light source.

13. The ocular characteristics measuring apparatus according to claim 1, wherein the apparatus recognizes whether the eye to be examined is an IOL eye.

* * * * *